（12）United States Patent
Niemiec et al.

(10) Patent No.: US 9,474,819 B2
(45) Date of Patent: Oct. 25, 2016

(54) METHOD OF ALTERNATINGLY EMITTING TWO OR MORE VOLATILE MATERIALS

(71) Applicant: S. C. Johnson & Son, Inc., Racine, WI (US)

(72) Inventors: Andrew N. Niemiec, Franklin, WI (US); Kenneth W. Michaels, Spring Grove, IL (US); Gopal P. Ananth, Racine, WI (US); Michael J. McGlade, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 432 days.

(21) Appl. No.: 14/012,632

(22) Filed: Aug. 28, 2013

(65) Prior Publication Data

US 2014/0064713 A1 Mar. 6, 2014

Related U.S. Application Data

(60) Provisional application No. 61/693,884, filed on Aug. 28, 2012.

(51) Int. Cl.
*A01G 13/06* (2006.01)
*A61L 9/03* (2006.01)

(52) U.S. Cl.
CPC ............. *A61L 9/035* (2013.01); *A61L 9/037* (2013.01); *A61L 2209/11* (2013.01)

(58) Field of Classification Search
None
See application file for complete search history.

(56) References Cited

U.S. PATENT DOCUMENTS

| 7,344,123 | B2 | 3/2008 | Pankhurst et al. |
| 8,119,064 | B2* | 2/2012 | Woo ............... A01M 1/2033 |
| | | | 239/34 |
| 2010/0294852 | A1 | 11/2010 | Banco et al. |
| 2011/0049259 | A1 | 3/2011 | Beland et al. |

FOREIGN PATENT DOCUMENTS

| GB | 2432789 A | 6/2007 |
| GB | 2444636 A | 6/2008 |
| WO | 2004093929 A2 | 11/2004 |

OTHER PUBLICATIONS

PCT/US2013/057093 International Search Report and Written Opinion dated Mar. 13, 2014.

* cited by examiner

*Primary Examiner* — Thor Campbell

(57) ABSTRACT

A method of alternatingly emitting two or more volatile materials comprises the steps of activating a first heater and emitting a first volatile material for a first period of time by emitting the first volatile material at a first primary evaporation rate and emitting the first volatile material at a first secondary evaporation rate after evaporation of the first volatile material at the first primary evaporation rate. The method further includes the steps of deactivating the first heater, activating a second heater, and emitting a second volatile material for a second period of time by emitting the second volatile material at a second primary evaporation rate and emitting the second volatile material at a second secondary evaporation rate after evaporation of the second volatile material at the second primary evaporation rate. The first and second secondary evaporation rates are less than the first and second primary evaporation rates.

18 Claims, 13 Drawing Sheets

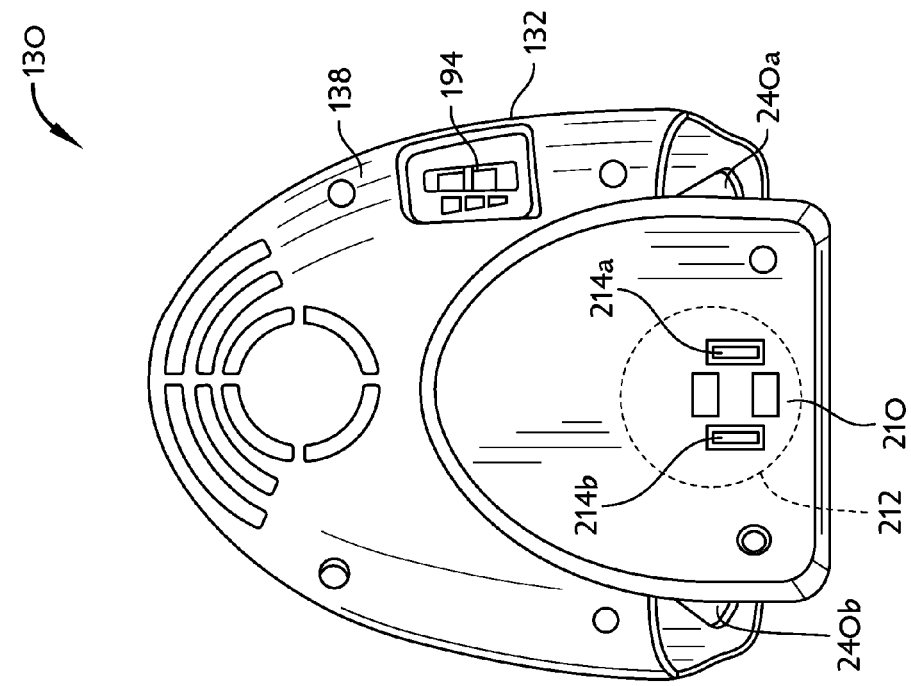

METHOD OF ALTERNATINGLY EMITTING TWO OR MORE VOLATILE MATERIALS

BACKGROUND

1. Field of the Disclosure

The present disclosure relates generally to a method of operating a volatile material dispenser and, more particularly, to a method of operating a volatile material dispenser having more than one volatile material.

2. Description of the Background

Various volatile material dispensers are known in the prior art and generally include a housing with a refill inserted therein. The refill generally includes a container for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the manner in which the volatile material is emitted, once the volatile material has been expended from the refill, the refill is removed by a user and replaced with a new refill.

One type of volatile material dispenser, sometimes referred to as a plug-in scented oil or plug-in dispenser, includes a housing and a heater disposed within the housing. A refill for use with a plug-in scented oil dispenser generally includes a container with a volatile material therein and a wick in contact with the volatile material and extending out of the refill. Upon insertion of the refill into the dispenser, at least a portion of the wick is disposed adjacent the heater such that volatile material that moves through the wick is volatilized by the heater. The plug-in dispenser typically includes a plug assembly having electrical prongs extending outwardly from the housing. The electrical prongs are inserted into a standard electrical outlet and thereafter supply electrical energy to the plug-in dispenser.

A refill for a plug-in dispenser may last up to a month or more. Some users of such dispensers desire a more frequent and/or automatic change in volatile material. Manufacturers of such devices have therefore begun selling plug-in dispensers including two heaters and adapted to hold two refills containing the same or different fragrances. The heaters are operated in an alternating fashion. In particular, a first of the heaters is activated for 45 minutes and, after 45 minutes has elapsed, the first heater is deactivated and a second of the heaters is activated for 45 minutes. Once the second 45 minute period has elapsed, the first heater is again activated and the pattern repeats until the device is turned off.

SUMMARY

In illustrative embodiments, a method of alternatingly emitting two or more volatile materials comprises the steps of activating a first heater to emit a first volatile material and emitting the first volatile material for a first period of time. Emitting the first volatile material includes the steps of emitting the first volatile material at a first primary evaporation rate and emitting the first volatile material at a first secondary evaporation rate after evaporation of the first volatile material at the first primary evaporation rate. The first secondary evaporation rate is less than the first primary evaporation rate. The method further includes the steps of deactivating the first heater, activating a second heater to emit a second volatile material, and emitting the second volatile material for a second period. Emitting the second volatile material includes the steps of emitting the second volatile material at a second primary evaporation rate and emitting the second volatile material at a second secondary evaporation rate after evaporation of the second volatile material at the second primary evaporation rate. The second secondary evaporation rate is less than the second primary evaporation rate. Still further, the method includes the steps of deactivating the second heater and repeating.

In illustrative embodiments, the step of activating the second heater may occur at the same time as or after the first heater has been deactivated.

In illustrative embodiments, the step of activating the second heater may occur before the first heater has been deactivated.

In illustrative embodiments, a variance between the first primary evaporation rate and the first secondary evaporation rate may be at least about 20% or a variance between the second primary evaporation rate and the second secondary evaporation rate may be at least about 20%.

In illustrative embodiments, the variance between the first primary evaporation rate and the first secondary evaporation rate may be at least about 25% or the variance between the second primary evaporation rate and the second secondary evaporation rate may be at least about 25%

In illustrative embodiments, the first and second time periods may each be between about 10 hours and about 50 hours.

In illustrative embodiments, the first and second time periods may each be between about 20 hours and about 40 hours.

In illustrative embodiments, a method of alternating emitting two or more volatile materials comprises the steps of activating a first heater to emit a first volatile material and emitting the first volatile material for a first time period of time. Emitting the first volatile material includes the steps of, during a first portion of the first time period, emitting the first volatile material such that a first primary room concentration is achieved and, during a second portion of the first time period, emitting the first volatile material such that a first secondary room concentration is achieved. The first secondary room concentration is less than the first primary room concentration and the first secondary room concentration occurs after the first primary room concentration. The method further includes the steps of deactivating the first heater, activating a second heater to emit a second volatile material, and emitting the second volatile material for a second time period of time. Emitting the second volatile material includes the steps of, during a first portion of the second time period, emitting the second volatile material such that a second primary room concentration is achieved and, during a second portion of the second time period, emitting the second volatile material such that a second secondary room concentration is achieved. The second secondary room concentration is less than the second primary room concentration and the second secondary room concentration occurs after the second primary room concentration. The method further includes the step of deactivating the second heater and repeating.

In illustrative embodiments, the step of activating the second heater may occur at the same time as or after the first heater has been deactivated.

In illustrative embodiments, the step of activating the second heater may occur before the first heater has been deactivated.

In illustrative embodiments, the room concentration of the first volatile material may peak at the first primary room concentration and trend downwardly until the first secondary room concentration at the point where the first heater is deactivated and the room concentration of the second volatile material may peak at the second primary room concentration and trend downwardly until the second secondary room concentration at the point where the second heater is deactivated.

In illustrative embodiments, a variance between the first primary room concentration and the first secondary room concentration may be at least about 1.0 mg/m$^3$ or a variance between the second primary room concentration and the second secondary room concentration may be at least about 1.0 mg/m$^3$.

In illustrative embodiments, the variance between the first primary room concentration and the first secondary room concentration may be at least about 1.4 mg/m$^3$ or a variance between the second primary room concentration and the second secondary room concentration may be at least about 1.4 mg/m$^3$.

In illustrative embodiments, an overall room concentration of the first volatile material and an overall room concentration of the second volatile material may be simultaneously at a level of greater than or equal to 0.5 milligrams per cubic meter for less than or equal to about 90% of the first time period and for less than or equal to about 90% of the second time period.

In illustrative embodiments, the overall room concentration of the first volatile material and the overall room concentration of the second volatile material may be simultaneously at a level of greater than or equal to 0.5 milligrams per cubic meter for less than or equal to about 50% of the first time period and for less than or equal to about 50% of the second time period.

In illustrative embodiments, a method of alternatingly emitting two or more volatile materials comprises the steps of activating a first heater to emit a first volatile material, emitting the first volatile material for a first time period, deactivating the first heater, and activating a second heater to emit a second volatile material. The second heater is activated prior to deactivation of the first heater, at the same time as deactivation of the first heater, or after deactivation of the first heater. The method further includes the steps of emitting the second volatile material for a second time period, deactivating the second heater, and repeating. Prior to repeating the step of activating the first heater, a room concentration of the first volatile material is reduced to a level of less than or equal to about 0.4 milligrams per cubic meter and, prior to repeating step (d), a room concentration of the second volatile material is reduced to a level of less than or equal to about 0.4 milligrams per cubic meter.

In illustrative embodiments, prior to repeating the step of activating the first heater, the room concentration of the first volatile material may be reduced to a level of less than or equal to about 0.2 milligrams per cubic meter and, prior to repeating step of activating the second heater, the room concentration of the second volatile material may be reduced to a level of less than or equal to about 0.2 milligrams per cubic meter.

In illustrative embodiments, the room concentration of the first volatile material and the room concentration of the second volatile material may be simultaneously at a level of greater than or equal to 0.5 milligrams per cubic meter for less than or equal to about 90% of the first time period and for less than or equal to about 90% of the second time period.

In illustrative embodiments, the room concentration of the first volatile material and the room concentration of the second volatile material may be simultaneously at a level of greater than or equal to 0.5 milligrams per cubic meter for less than or equal to about 50% of the first time period and for less than or equal to about 50% of the second time period.

BRIEF DESCRIPTION OF THE DRAWINGS

FIG. 2 is a front isometric view of the volatile material dispenser of FIG. 1;

FIG. 3 is a rear elevational view of the dispenser of FIG. 1;

Other aspects and advantages of the present disclosure will become apparent upon consideration of the following detailed description, wherein similar structures have like or similar reference numerals.

DETAILED DESCRIPTION

The present disclosure is directed to methods of operating volatile material dispensers adapted to dispenser more than one volatile material. While the methods of the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 1:
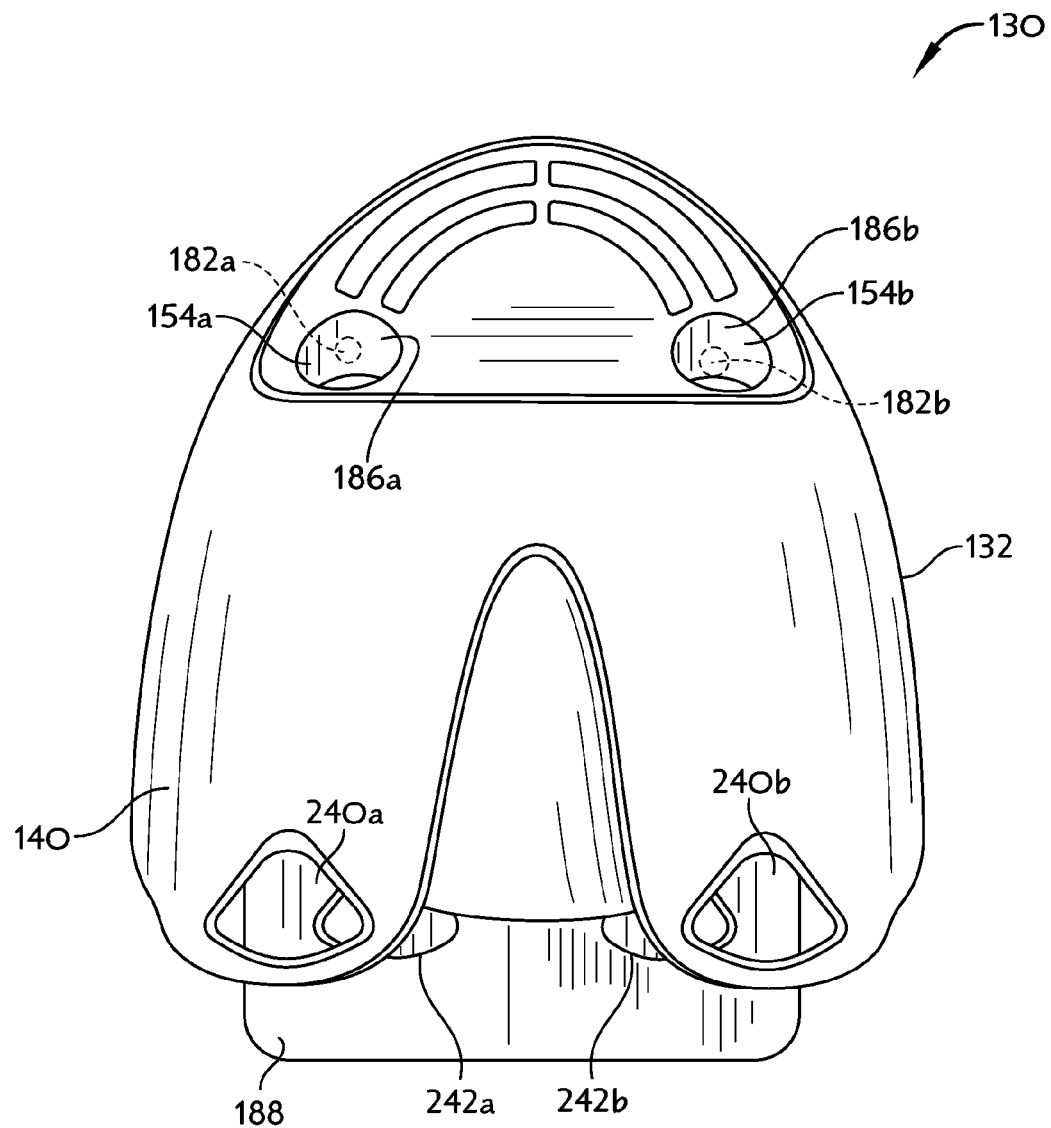
FIG. 1 is a front elevational view of a volatile material dispenser for implementing the methods of the present disclosure.
Figure 4:
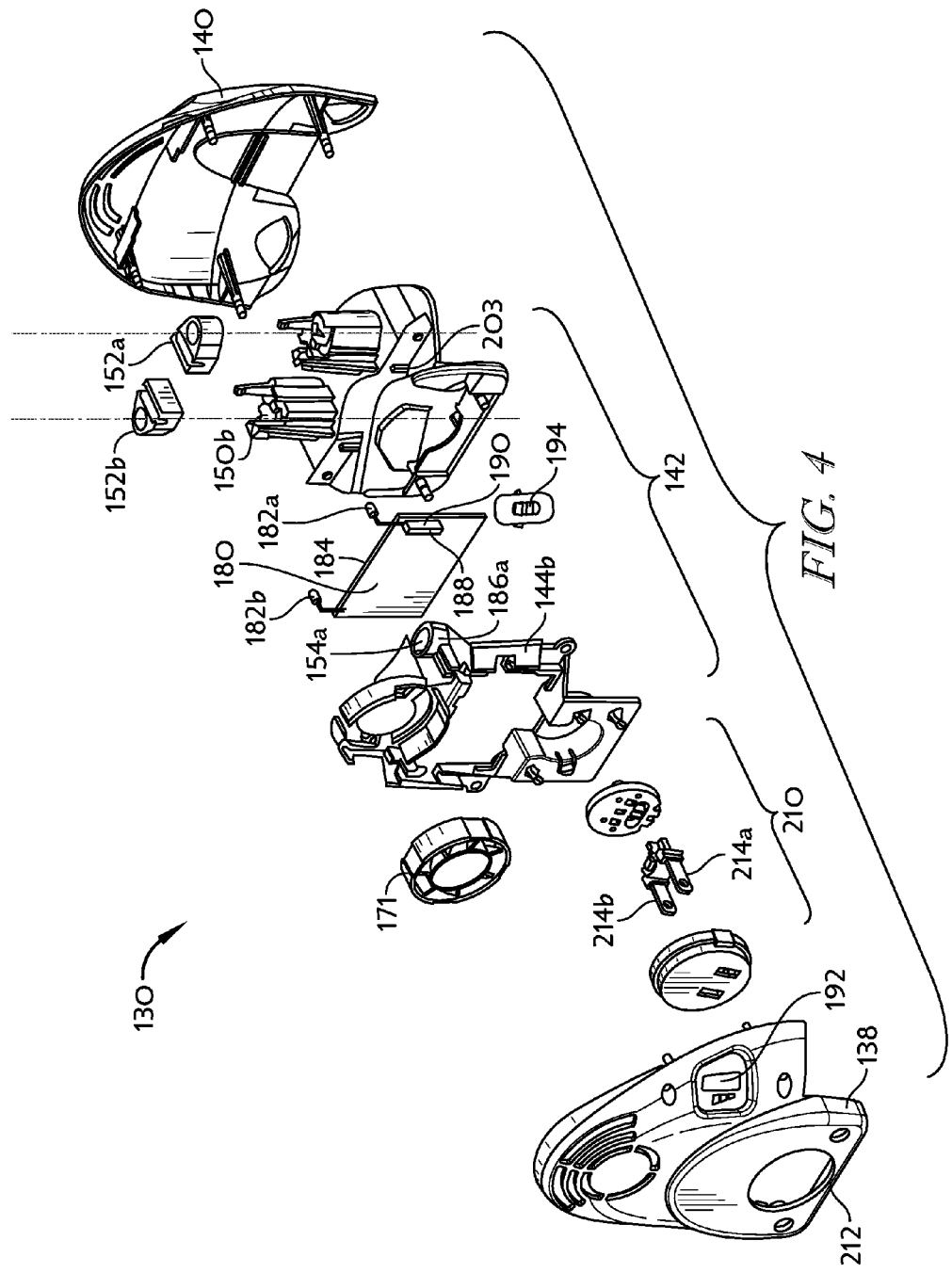
FIG. 4 is an exploded view of the dispenser of FIG. 1.

Referring to the drawings, a volatile material dispenser 130 is depicted in FIGS. 1-4. The operation of the dispenser 130 will be discussed in greater detail below. As seen in FIGS. 1 and 2, the dispenser 130 includes a housing 132 for holding two containers 134a, 134b having volatile materials 135a, 135b therein and wicks 136a, 136b extending therefrom. As best seen in FIG. 4, the housing 132 includes a rear portion 138, a cover portion 140, and a mounting structure 142. The mounting structure 142 is attached to the rear portion 138 and the cover portion 140 is mounted to the rear portion 138 and the mounting structure 142 such that the mounting structure 142 is disposed between the rear and cover portions 138, 140.

Still referring to FIG. 4, the mounting structure 142 includes front and rear portions 144a, 144b, wherein the front portion 144a includes a horizontal surface 146 having first channels 150a, 150b extending therethrough, ring heaters 152a, 152b disposed atop structures forming the first channels 150a, 150b, and second channels 154a, 154b positioned over the ring heaters 152a, 152b. The heaters 152a, 152b are disposed above the first channels 150a, 150b, and the second channels 154a, 154b are disposed above the heaters 152a, 152b. A fan 171 may optionally be provided within the rear portion 144b of the mounting structure 142.

As seen in FIG. 4, a printed circuit board (PCB) 180 is secured within the rear portion 144b of the mounting structure 142 and includes circuitry to control the dispenser 130. Light emitting diodes (LEDs) 182a, 182b extend from an upper edge 184 of the PCB 180 and are disposed adjacent rear surfaces 186a, 186b of the second channels 154a, 154b. The LEDs 182a, 182b may be illuminated when respective heaters 152a, 152b are actuated. Optionally, any feature known in the art may be utilized to indicate which heater 152a, 152b is in operation.

Still referring to FIG. 4, an intensity level switch 188 extends from the PCB 180 and includes an actuator arm 190 that extends through an aperture 192 in the rear portion 138 of the housing 132 to allow for varying an intensity level of the volatile materials 135a, 135b. A button 194 is disposed over the actuator arm 190 to change a position of the switch 188, as seen in FIG. 3.

Alternatively, or in addition to the intensity level switch 188, a volatile material selector switch (not shown) or another type of switch may be utilized. The volatile material selector switch would allow a user to select to emit a first of the volatile materials 135a, a second of the volatile materials 135b, or both of the volatile materials 135a, 135b in an alternating sequence, as will be discussed in greater detail below.

The intensity level switch 188 and/or selector switch may alternatively provide other functionalities to the dispenser 130. For example, either switch (or an additional switch) may allow a user to manually interrupt operation of an operating cycle and switch to the other of the heaters 152a, 152b at any time during an operating cycle. Any number of switches providing any number of different functionalities to the dispenser 130 may be utilized.

As seen in FIG. 4, a plug assembly 210 is connected to the rear portion 144b of the mounting structure 142 and extends through an aperture 212 in the rear portion 138 of the housing 132. Electrical blades 214a, 214b of the plug assembly 210 are inserted into an electrical socket to power the dispenser 130.

The containers 134a, 134b, as seen in FIG. 2, are inserted into the dispenser 130 by inserting portions of the wicks 136a, 136b that extend out of the respective containers 134a, 134b through the first channels 150a, 150b and the ring channels 156a, 156b, respectively, such that the wicks 136a, 136b reside in same and gaps are formed between the wicks 136a, 136b and walls forming the first channels 150a, 150b and the ring channels 156a, 156b. The containers 134a, 134b may be held within the dispenser 130 in any manner known in the art, for example, by way of mating projections 244a, 244b and apertures 240a, 240b and/or grooves 242a, 242b.

The dispenser 130 of FIGS. 1-4 is shown and discussed in greater detail in co-pending Porchia et al. U.S. application Ser. No. 12/288,606, filed Oct. 22, 2008, and entitled "Volatile Material Diffuser and Method of Preventing Undesirable Mixing of Volatile Materials."

The dispenser 130, or any other dispenser for emitting multiple volatile materials, may be programmed to alternatingly emit two fragrances located in the containers 134a, 134b. In particular, a first of the fragrances is emitted from the container 134a for a first period of time by activating the heater 152a. The heater 152a is deactivated after the first period of time and the heater 152b is activated for a second period of time to emit a second of the fragrances from the container 134b. The heater 152b is deactivated after the second period of time and the heater 152b is again activated to emit the first fragrance for the first period of time and the first and second fragrances are continuously alternated in this manner.

The first and second time periods are preferably greater than 10 hours. The first and second periods may be greater than or equal to 10 hours, 12 hours, 16 hours, 20 hours, 24 hours, 25 hours, 50 hours, 100 hours, one week, two weeks, one month, or any time period greater than 10 hours. Still optionally, the first and second periods may be a range including end points selected from any of the time periods disclosed herein. In illustrative embodiments, a user may have an option of selecting the first and/or second time periods from two or more time periods (for example, using a switch). In one illustrative embodiment, each of the first and second time periods may be selected from a time period of either about 25 hours or about 7 days.

The first and second time periods may be the same or may be different. In a first example, each of the first and second time periods is about 24 hours or about 25 hours. In another example, a first fragrance is emitted for 2 days that correspond to the days of the weekend and a second fragrance is emitted for 5 days that correspond to the days of the work week. The same time periods may be utilized for dispensers including more than two fragrances.

In some embodiments, the heater 152a may be deactivated at the same time the heater 152b is activated and the heater 152b may be deactivated at the same time the heater 152a is activated. In other embodiments, a rest period may follow deactivation of each of the heaters 152a, 152b and proceed activation of the other of the heaters 152a, 152b. In this manner, no fragrance is emitted during the rest period, thereby allowing the fragrance emitted prior to the rest period to partially or fully dissipate before emission of the next fragrance. The rest period may be 1 hour or greater. In particular embodiments, the rest period may be 1 hour, 2 hours, 4 hours, 8 hours, 12 hours, or 24 hours depending on a length of emission of each fragrance. In still other embodiments, each heater 152a, 152b may be activated prior to deactivation of the other heater 152a, 152b, thereby creating an overlap period. The overlap period may be 1 hour or greater. In particular embodiments, the overlap period may be 1 hour, 2 hours, 4 hours, 8 hours, 12 hours, or 24 hours depending on a length of emission of each fragrance.

As noted above, prior art dispensers for multiple volatile materials, for example fragrances, alternatingly emit the fragrances for 45 minutes each. Manufacturers believe that alternating emission for short time periods of 45 minutes prevents habituation. In particular, manufacturers of some of such devices perceive that, after a short period of time, a user becomes so accustomed to an emitted fragrance that they no longer perceive or smell the fragrance. They therefore feel that alternating periods of 45 minutes refresh the fragrances and allow a user to smell a different fragrance every 45 minutes, thereby preventing habituation.

While alternatingly emitting fragrances for 45 minutes may aid in overcoming habituation, such time periods are not desirable. Through consumer panels and other testing, the assignee of the present application has discovered that users do not desire shorter periods of emission, for example, 45 minutes. Specifically, users select fragrances that they like and they want to enjoy the fragrances they have selected, not some combination of fragrances that may or may not be desirable. Shorter periods of emission are perceived as causing undesirable mixing of fragrances within a space. For example, once a heater associated with a particular fragrance is deactivated, that fragrance does not automatically dissipate from the space. Rather, the fragrance takes time to dissipate, thereby mixing with the next emitted fragrance. It is the perception of users that 45 minute and other relatively short time periods, in general, are not long enough to allow a previously emitted fragrance to dissipate and still allow the next emitted fragrance to be sensed by itself for a period of time long enough for the user to enjoy the fragrance. Instead, the user smells a combination of fragrances during a majority or all of each 45 minute emission period. The user therefore is unable to enjoy the individual fragrances they desired and purchased.

If mixing of fragrances occurs in the embodiments disclosed herein, the time periods for emission of each fragrance are long enough to allow the previously emitted fragrance to dissipate and allow the user to enjoy each fragrance for a period of time. If rest periods are utilized between the emission of fragrances, less mixing or no mixing of fragrances occurs, thereby increasing the enjoyment of the individual fragrances by a user.

A benefit of minimizing or eliminating the time during which fragrances are mixed is that users can select fragrances that are not necessarily compatible. Specifically, packages of two refills having compatible fragrances are currently sold for some dispensers for emitting two volatile materials. This limits the fragrance combinations for selection by a user. If mixing is minimized, there is little need to worry about having compatible fragrances and, therefore, individual refills may be sold for selection by a user. This provides a wider range of options for a user.

Users also like to conceptually associate different fragrances with different time periods. Utilizing the emission periods disclosed herein, the user will know what fragrance is emitted at any particular time. The emission period for each fragrance may be a period of time that a user can comprehend or quantify. For example, if each fragrance is emitted for 24 hours, the user understands that each day they will smell a different fragrance. Similarly, in the example above where one fragrance is emitted on the weekend and the other during the work week, the user understands when the different fragrances will begin and end. In another example, fragrances may be alternated every 12 hours, for example, by providing a first distinct fragrance during the day and a second distinct fragrance at night. In contrast, when utilizing an emission period of 45 minutes, the user cannot correlate the 45 minutes to any standard or comprehendible time period and, thus, does not understand when each of the fragrances will be emitted or when the dispenser switches from one fragrance to the other.

Consumer Testing

Figure 5B:
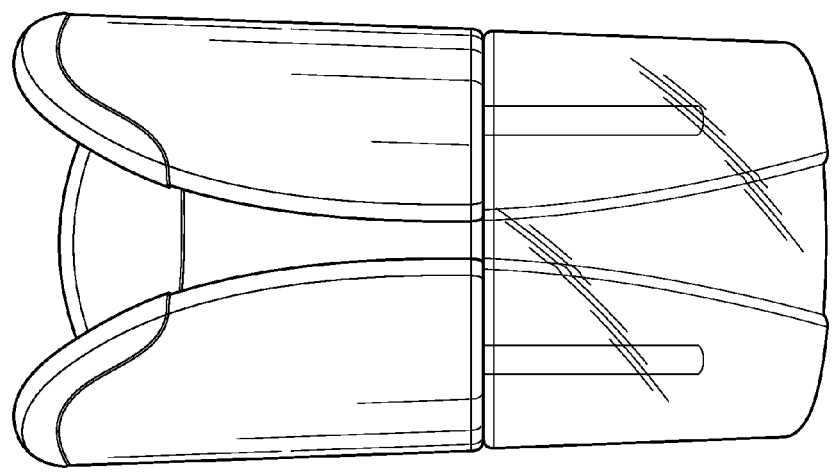
FIG. 5B is a second volatile material dispenser used for consumer testing.
Figure 5A:
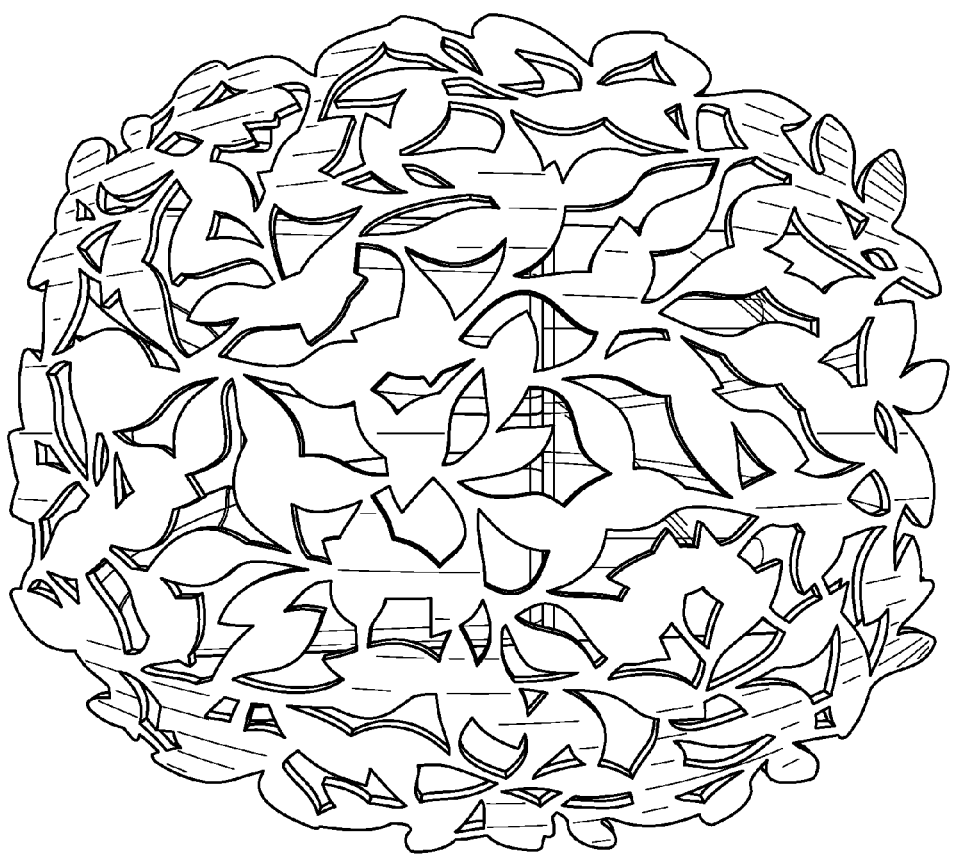
FIG. 5A depicts a first volatile material dispenser similar to the dispenser of FIGS. 1-4 and which was used for consumer testing.

Consumer testing was conducted in which first and second volatile material dispensers were tested in-home by 314 consumers. The first dispenser, as seen in FIG. 5A, is similar to that disclosed in FIGS. 1-4 herein. The first dispenser employed an algorithm in which two fragrances were alternated and each of the fragrances was emitted for 25 hours. The fragrances were emitted by alternatingly activating and deactivating heaters corresponding to the fragrances. Each heater was deactivated 5 minutes after activation of the other heater. The dispenser of FIG. 5A is described in greater detail in Gordon et al., U.S. application Ser. No. 13/667,157, titled "Volatile Material Dispenser Having a Faceplate". The second dispenser, as seen in FIG. 5B, was a dispenser sold by Procter & Gamble under the Febreze® Noticeables® tradename. The Noticeables® device is commercially available and employs an algorithm in which two fragrances are alternated and each of the fragrances is emitted for 45 minutes. A heater associated with the first fragrance is deactivated at the same time a heater associated with the second fragrance is activated. Similarly, the heater associated with the second fragrance is deactivated at the same time the heater associated with the first fragrance is activated.

The consumers were asked to use both dispensers in their homes for a period of four (4) weeks. The study was balanced between main room placement and secondary room placement to eliminate room placement bias. Respondents or consumers were asked a number of questions regarding their opinions and experiences with both the first and second dispensers. The study consisted of 314 respondents split between two cells. In a first cell, consumers were given the first dispenser with two refills, one containing the Glade® Hawaiian Breeze fragrance and the other containing the Glade® Sunny Days fragrance. The consumers in the first cell were also given the second dispenser with a pair of refills sold as Febreze® Hawaiian Aloha. In a second cell, consumers were given the first dispenser with two refills, one containing the Glade® Apple Cinnamon fragrance and the other containing the Glade® Lavender Peach Blossom fragrance. The consumers in the second cell were also given the second dispenser with a pair of refills sold as Febreze® Meadows and Rain. Each of the consumers was asked the following question with respect to each of the first and second dispensers at day three, week two, and week four:

What best describes your initial opinion of the "fragrance experience" provided by the product over the past few days? By "fragrance experience" we mean the type of fragrance, the fragrance strength, and how fragrance lasted.

Figure 6A:
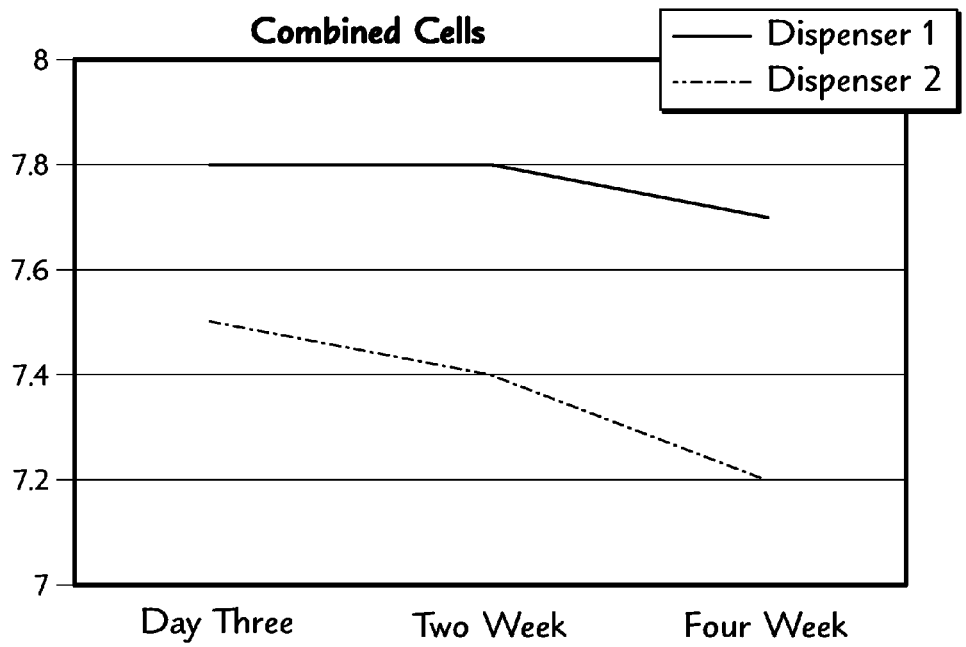
FIGS. 6A-6C are graphs depicting ratings for "fragrance experience" for the first and second volatile material dispensers of FIGS. 5A and 5B during the consumer testing.
Figure 6B:
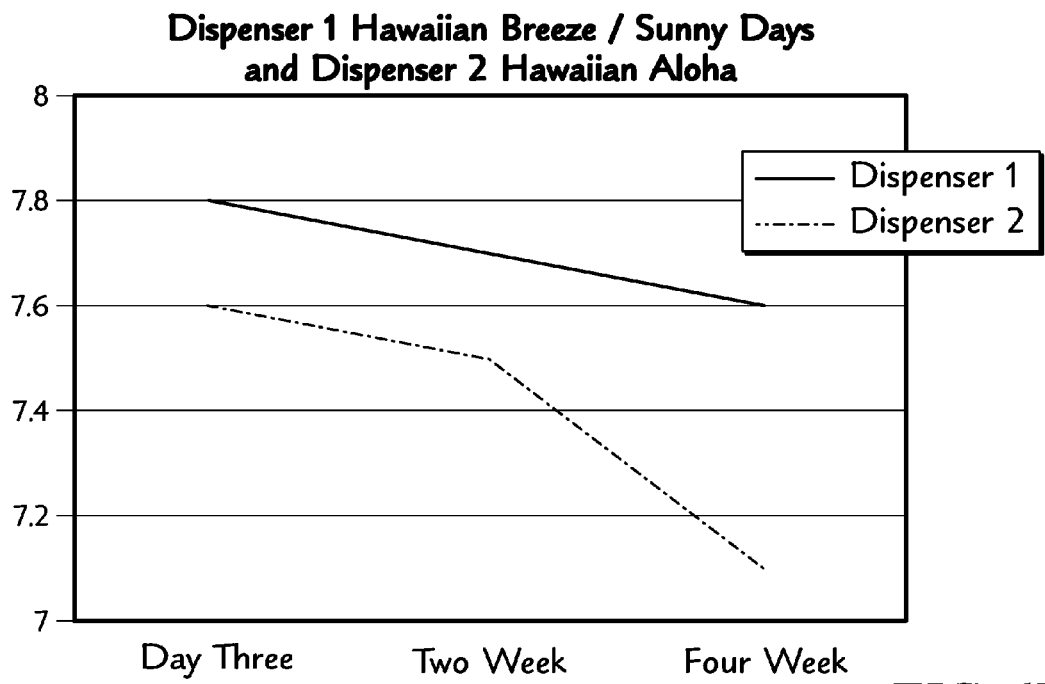

Each of the consumers was then asked to rate each of the dispensers on a scale of 1 to 9 after three days, two weeks, and four weeks. As seen in FIG. 6A, the average "fragrance experience" for the first and second cells combined (314 respondents) for the first dispenser was at 7.8 at day three, 7.8 at week two, and 7.7 at week four. The average "fragrance experience" for both cells for the second dispenser was 7.5 at day three, 7.4 at week two, and 7.2 at week four.

As seen in 6B, the average "fragrance experience" of the first dispenser in the first cell was at 7.8 at day three, 7.7 at week two, and 7.6 at week four. The average "fragrance experience" of the second dispenser in the first cell was 7.6 at day three, 7.5 at week two, and dipped down to 7.1 at week four. Overall, the "fragrance experience" for the first dispenser was better than the "fragrance experience" for the second dispenser.

Figure 6C:

Referring to FIG. 6C, the average "fragrance experience" of the first dispenser in the second cell was 7.8 for day three, 7.9 for week two, and 7.7 for week four. The average "fragrance experience" of the second dispenser in the second cell was 7.5 for day three, 7.4 for week two, and 7.2 for week four. Similar to the first cell of testing, in the second cell of testing, the "fragrance experience" for the first dispenser was better than the "fragrance experience" for the second dispenser.

Figure 7A:
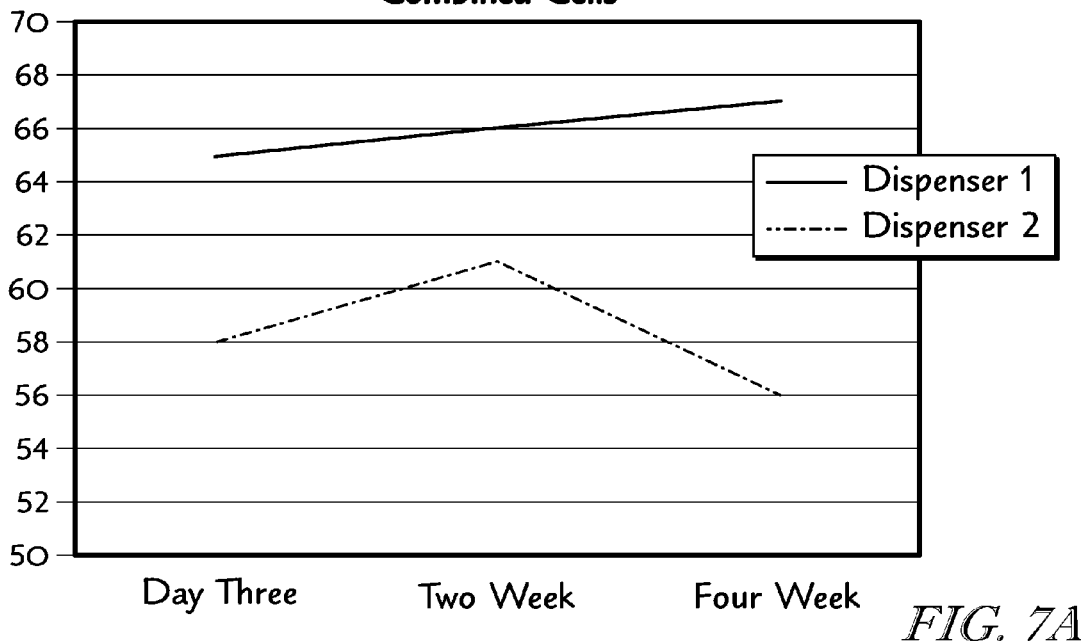
FIGS. 7A-7C are graphs depicting ratings for fragrance strength for the first and second volatile material dispensers of FIGS. 5A and 5B during the consumer testing.

In the first and second cells of testing, the consumers were asked the question with respect to each of the dispensers: "How do you feel about the strength of this fragrance?" The consumers answered this question by selecting from the answers: (1) much too weak, (2) somewhat too weak, (3) "just right", (4) somewhat too strong, and (5) much too strong. The graphs of FIGS. 7A-7C track the number of consumers who responded that the strength of the fragrance was "just right" for each dispenser. As seen in FIG. 7A, which shows the results for the first and second cells combined (314 respondents), 65% of the consumers responded that the strength of the fragrance from the first dispenser was "just right" at day three, 66% responded that the strength of the fragrance was "just right" at week two, and 67% responded that the strength of the fragrance was "just right" at week four. In addition, 58% of the consumers responded that the fragrance from the second dispenser was "just right" at day three, 61% responded that the fragrance was "just right" at week two, and 56% responded that the fragrance was "just right" at week four.

Figure 7B:
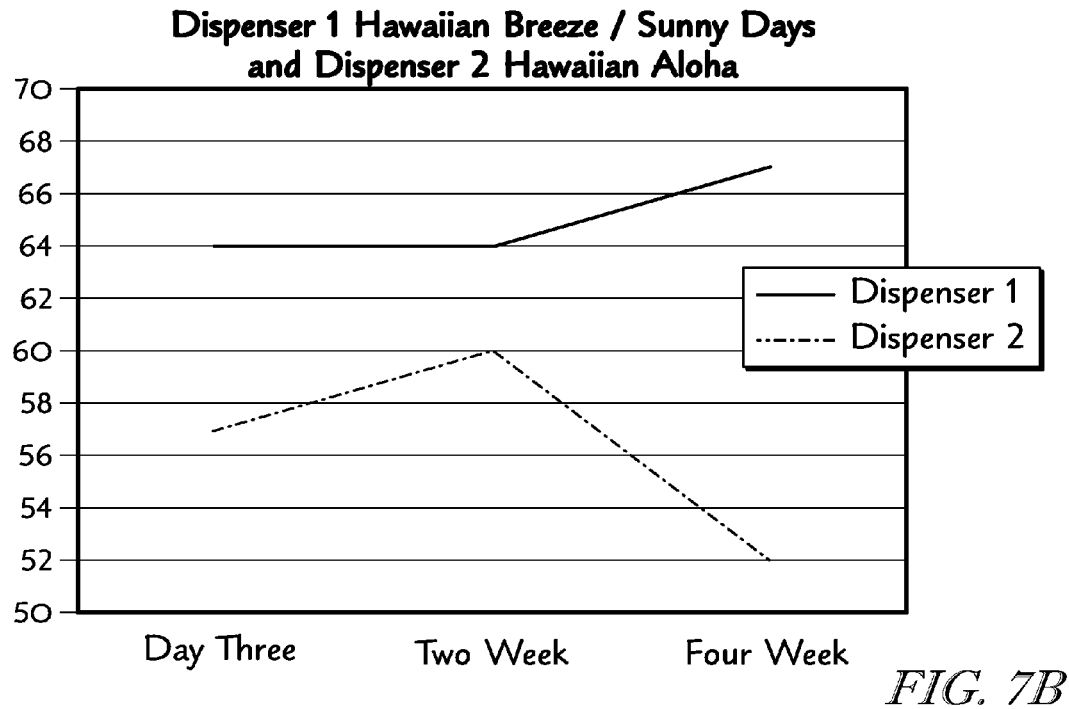

As seen in FIG. 7B, in the first cell of testing, 64% of the consumers responded that the strength of the fragrance from the first dispenser was "just right" at day three and week two and 67% of the consumers responded that the strength of the fragrance from the first dispenser was "just right" at week four. In addition, 57% of the consumers responded that the strength of the fragrance from the second dispenser was "just right" at day three, 60% responded that the fragrance from the second dispenser was "just right" at week two, and 52% responded that the fragrance from the second dispenser was "just right" at week four. In summary, more consumers preferred the strength of the fragrance from the first dispenser than the strength of the fragrance from the second dispenser.

Figure 7C:
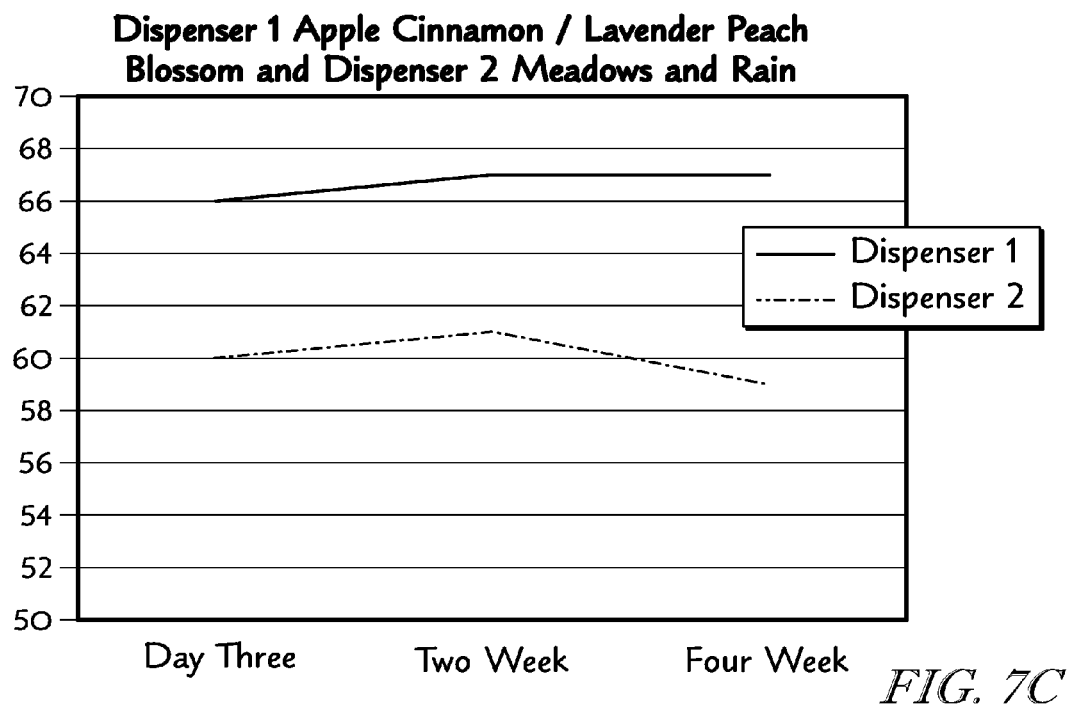

Referring to FIG. 7C, in the second cell of testing, 66% of the consumers responded that the strength of the fragrance from the first dispenser was "just right" at day three and 67% responded that the strength of the fragrance from the first dispenser was "just right" at week two and week four. In addition, 60% of the consumers responded that the strength of the fragrance from the second dispenser was "just right" at day three, 61% responded that the fragrance from the second dispenser was "just right" at week two, and 59% responded that the fragrance from the second dispenser was "just right" at week four. Similar to the first cell, more consumers preferred the strength of the fragrance from the first dispenser than the strength of the fragrance from the second dispenser.

The consumers in both cells (314 respondents) were asked whether they preferred the "fragrance experience" of the first dispenser or the "fragrance experience" of the second dispenser. At week two, 65% of the consumers responded that they preferred the first dispenser and, at week four, 67% of the consumers responded that they preferred the first dispenser.

Simulating Performance Via Computer Model

Figure 8A:
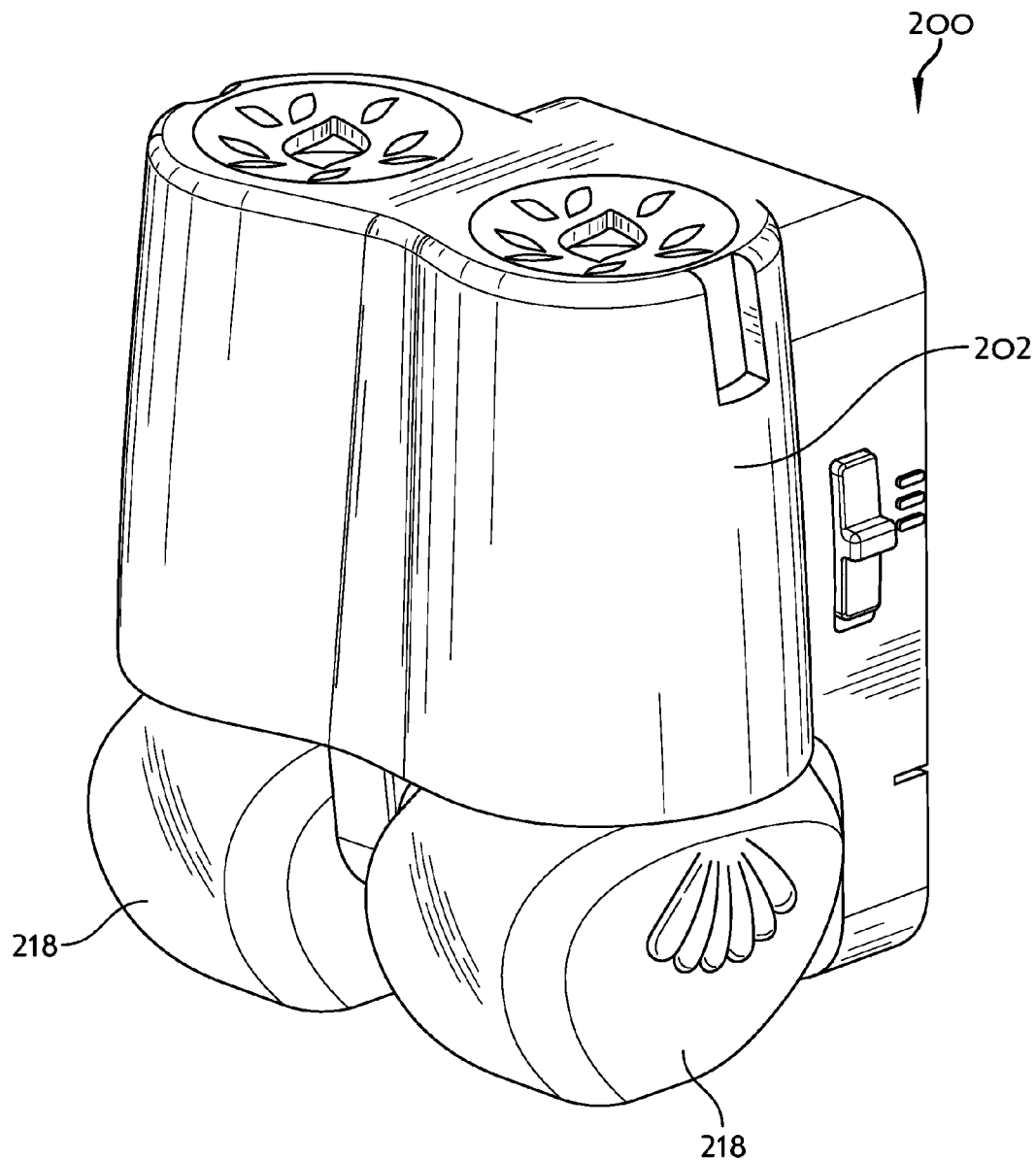
FIG. 8A is a top perspective view of a volatile material dispenser used in a computer modeling simulation.
Figure 8B:
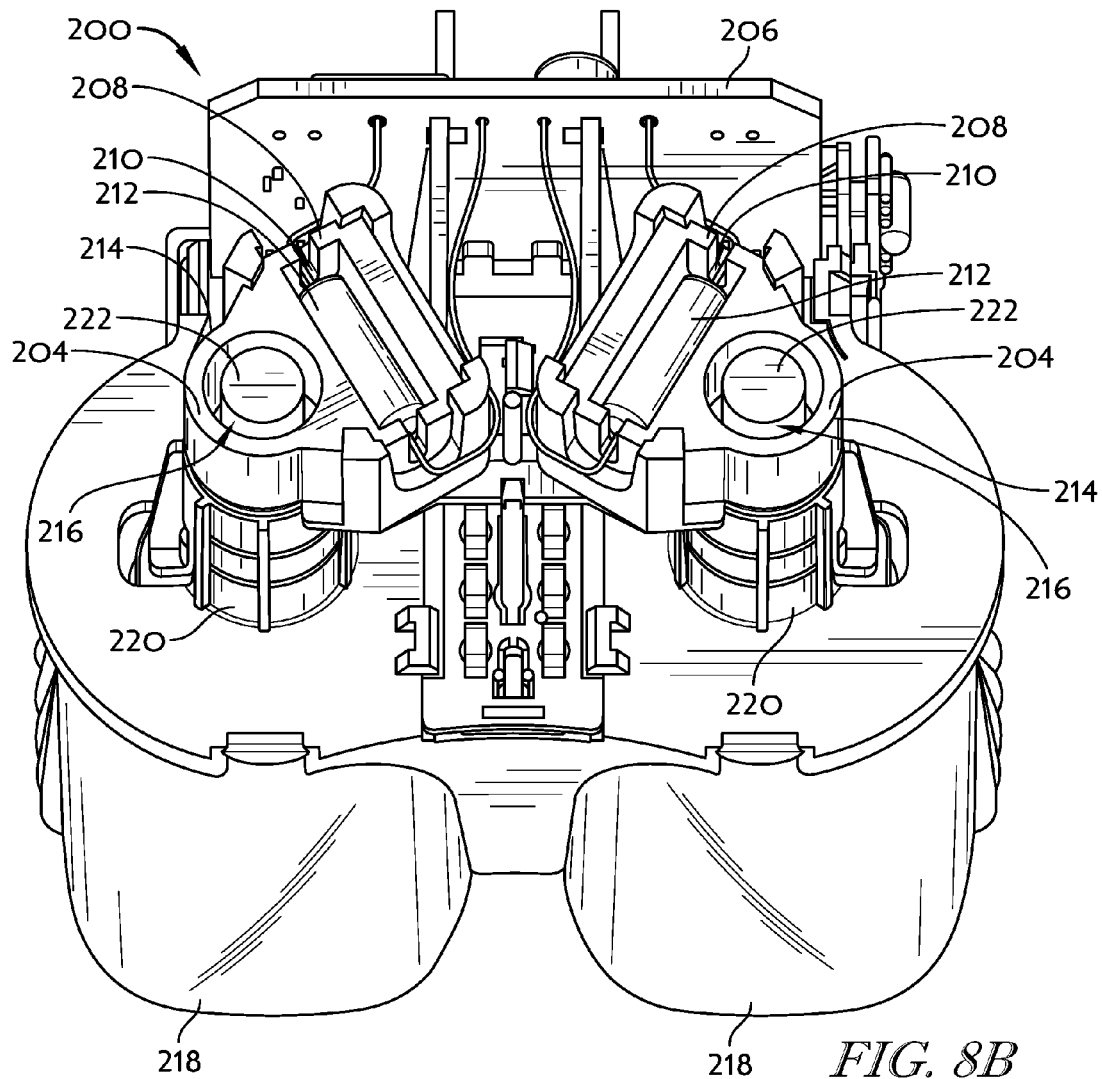
FIG. 8B is a top perspective view of the volatile material dispenser of FIG. 8A with a housing thereof removed and depicting two heating blocks for heating wicks extending from corresponding refills.

Using ANSYS Fluent three dimensional software, a computational fluid dynamics (CFD) model was created. The three dimensional model was created using an actual volatile material dispenser 200, as seen in FIGS. 8A and 8B. The dispenser 200 includes a housing 202 that is adapted to be connected to a conventional electrical outlet. Two heating blocks 204 are electrically connected to a circuit board 206, which powers the dispenser 200. Each heating block 204 includes a rectangular section 208 having a cavity 210 that holds a heating element 212 and a circular section 214 having a channel 216 therethrough.

The dispenser 200 accommodates two refills 218, which are modeled after a refill sold by S.C. Johnson & Son, Inc. under Glade® Plugins® Scented Oil. The dispenser 200 includes channels 220 through which wicks 222 of the refills 218 are inserted. The wicks 222 are inserted through the channels 220 and into the channels 216 in the heating blocks 204 to heat ends of the wicks 222 and vaporize volatile material with the wicks 222. The refills 218 are retained within the dispenser 200 in any suitable manner.

The three dimensional model of the dispenser 200 of FIGS. 8A and 8B was made. The model suitably depicts the components, relative placement of components, and the dimensions of the dispenser 200. The CFD model is a transient model with a multi-domain and multi-species approach. A first domain comprises the air and the wick, wherein a quasi-steady formulation for energy in an air-wick domain allows for multi-component free convention. The first domain also includes radiation heat transfer effects. A second domain comprises multi-component oil transport and evaporation within the wick and the reservoir, as well as the transient multi-component liquid convention diffusion in the wick.

Each heating block 204 was constructed of ceramic having a thermal conductivity of 2 Watts/meter-Kelvin (W/m-K), a density of 2000 kilograms/cubic meter (kg/m$^3$), and a heat capacity of 800 Joules per kilogram-Kelvin (J/kg-K). The dispenser 200 was formed of a high density polypropylene having a thermal conductivity of $k(T)=-1.654683+1.728236E-2*T-5.595958E-5*T^2+8.080327E-8*T^3-4.317061E-11*T^4$, a density of 925 kg/m$^3$, and a heat capacity of 2500 J/kg-K. Other materials used in the dispenser 200 were standard materials, such as copper. The wicks 222 within the refills 218 had a porosity of 0.6.

The CFD model included fragrances comprised of mixtures of n alkanes $(C(N)H(2*N+2))$. Two distinct fragrance mixtures were used, each containing five different alkanes: C9, C11, C13, C15, and C17, which physical properties, such as vapor pressure, of components in typical fragrances. Each fragrance mixture has identical thermodynamic properties. The characteristics of the alkanes are included in Tables 1 and 2 below.

TABLE 1

Molecular Weight, A, B, C, and D (for determining Vapor Pressure)

| Species Name | N | Molecular Weight (kg/kmol) | A (unitless) | B (K) | C (unitless) | D (1/K$^2$) |
|---|---|---|---|---|---|---|
| Nonane | 9 | 128 | −8.3274E+00 | −7.7394E+03 | 7.2547E+01 | 3.8948E−06 |
| Undecane | 11 | 156 | −1.7372E+01 | −1.1585E+04 | 1.3409E+02 | 9.4533E−06 |
| Tridecane | 13 | 184 | −1.2304E+01 | −1.0992E+04 | 1.0162E+02 | 4.9582E−06 |

TABLE 1-continued

Molecular Weight, A, B, C, and D (for determining Vapor Pressure)

| Species Name | N | Molecular Weight (kg/kmol) | A (unitless) | B (K) | C (unitless) | D (1/K^2) |
|---|---|---|---|---|---|---|
| Pentadecane | 15 | 212 | −2.4792E+01 | −1.6463E+04 | 1.8781E+02 | 1.0974E−05 |
| Heptadecane | 17 | 240 | 3.5039E+01 | −2.1229E+04 | | 1.5311E−05 |

TABLE 2

Minimum and Maximum Temperatures and Mass Fraction

| Species Name | Tmin (K) | Range of validity Tmax (K) | INITIAL LIQUID COMPOSITION MASS FRACTION |
|---|---|---|---|
| Nonane | 219.63 | 595.65 | 0.0361 |
| Undecane | 247.57 | 638.76 | 0.3264 |
| Tridecane | 267.76 | 675.8 | 0.4693 |
| Pentadecane | 283.1 | 706.8 | 0.0382 |
| Heptadecane | 285.13 | 733.37 | 0.1300 |

In order to calculate the evaporation rate of each fragrance mixture, a vapor pressure of each component was calculated using the gas species vapor pressure shown below:

$$Pvap(T) \text{in[Pa]} = 1000 * \exp(A * \ln(T) + B/T + C + D*T*T)$$

where A, B, C, and D are constants, as seen in Table 1.

The CFD model was used to measure evaporation rate and room concentration. While the CFD model was a simulation, one skilled in the art would understand how to measure evaporation rate and room concentration, either in real life or computer modeling. For example, evaporation rate may be calculated by standard weight loss measurements or other suitable methods, as are known to those skilled in the art. Similarly, room concentration may be calculated by any number of measurement techniques and devices, as are well known in the art, for example, by using gas chromatography—mass spectrometry and/or using models using standard air change rates and at normal household operating conditions.

Figure 9:
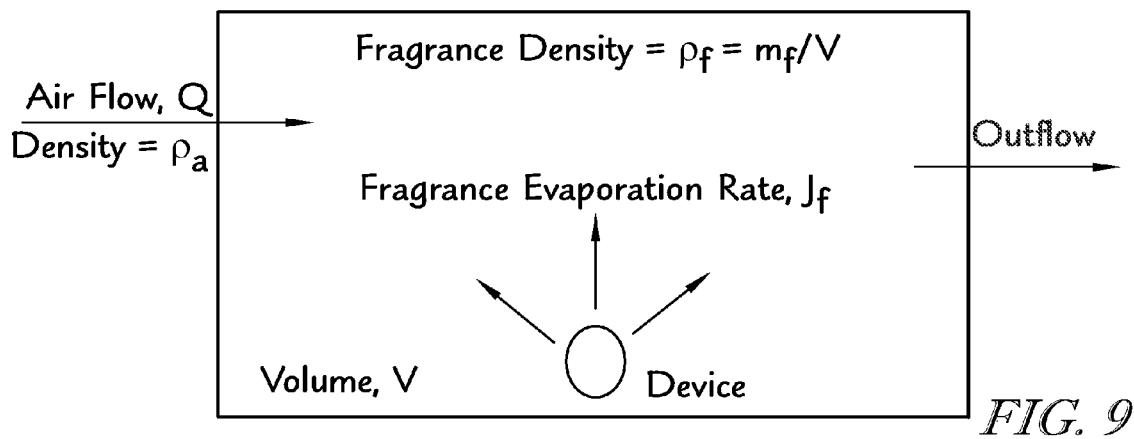
FIG. 9 is a graphical depiction of a room concentration model for the computer modeling simulation.

A room concentration model was created assuming a well-mixed flow and a dilute approximation using mass flow (device)<<mass flow (air through the room). The room concentration model is shown in FIG. 9. A room size of approximately 28 cubic meters (or approximately 988 cubic feet, 10 feet by 12 feet by 8.25 feet) was used, which represents a typical home room size. In addition, an air change rate of 0.5 changes per hour was used, which represents a typical home passive air change rate. The shape of a room concentration curve (see, for example, FIGS. 12 and 13) will vary based on the room size and the air change rate. The equation governing room concentration for the CFD model is:

$$\frac{d\rho_f}{dt} = \frac{1}{V}(-\rho_f Q + N_f) \quad \text{Equation 1}$$

Where Q/V=0.5 air changes per hour and an initial condition of:

Initial Condition:

$$\rho_f(t=0) = 0$$

$N_f$ is determined from a dual-device evaporation model. The room concentration equation is solved for each wick separately, as it is assumed that the fragrances are unique.

The room concentration equations for each fragrance are then integrated using weighted differencing:

$$\frac{\rho_f^{k+1} - \rho_f^k}{\Delta t} = \frac{1}{V}[\beta(-\rho_f^{k+1}Q + N_f^{k+1}) + (1-\beta)(-\rho_f^k Q + N_f^k)] \quad \text{Equation 2}$$

Where k and k+1 represent data at the time t and the future time at (t+Δt). β is allowed to vary between 0 and 1, wherein 0=fully explicit and 1=fully implicit. β=0.5 yields Crank Nicolson, which is $2^{nd}$ order accurate in time. Solving Equation 2 yields:

$$\rho_f^{k+1} = \frac{\rho_f^k + \beta \Delta t N_f^{k+1}/V + (1-\beta)\Delta t(-\rho_f^k Q/V + N_f^k/V)}{(1 + \beta \Delta t Q/V)} \quad \text{Equation 3}$$

Using the CFD model, two types of data were tracked: (1) evaporation rate versus time and (2) room concentration versus time. Various time periods were used for each type of data. During each time period, a first of the heating blocks was actuated for a first period of time and, after the first period of time, the heating block was deactivated. At the same time the first heating block was deactivated, the second heating block was activated for a second period of time. After the second period of time elapsed, the second heating block was deactivated and the first heating block was simultaneously activated and the heating of the first and second heating blocks was alternated in this fashion. The first and second time periods were the same and were tested at: (A) 45 minutes, (B) 2 hours, (C) 10 hours, (D) 25 hours, (D) 50 hours, (E) 100 hours, and (F) 1000 hours or continuous emission. A power rating for each heater during activation was about 1.8 watts.

Figure 10:
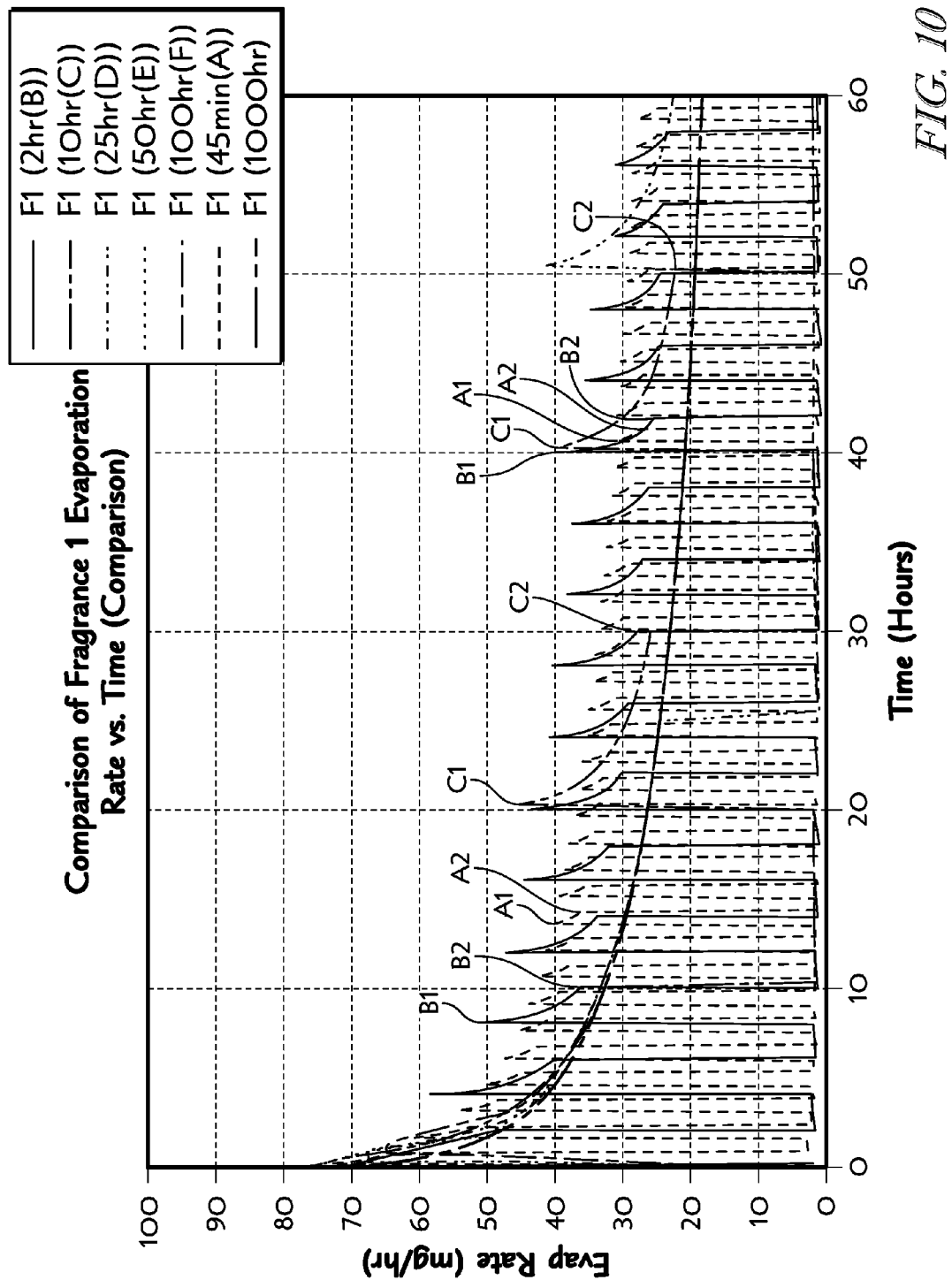
FIG. 10 is a graph depicting evaporation rate (in milligrams per hour) versus time (in hours) for alternating time periods of 45 minutes, 2 hours, 10 hours, 25 hours, 50 hours, 100 hours, and 1000 hours for a single fragrance.
Figure 11:
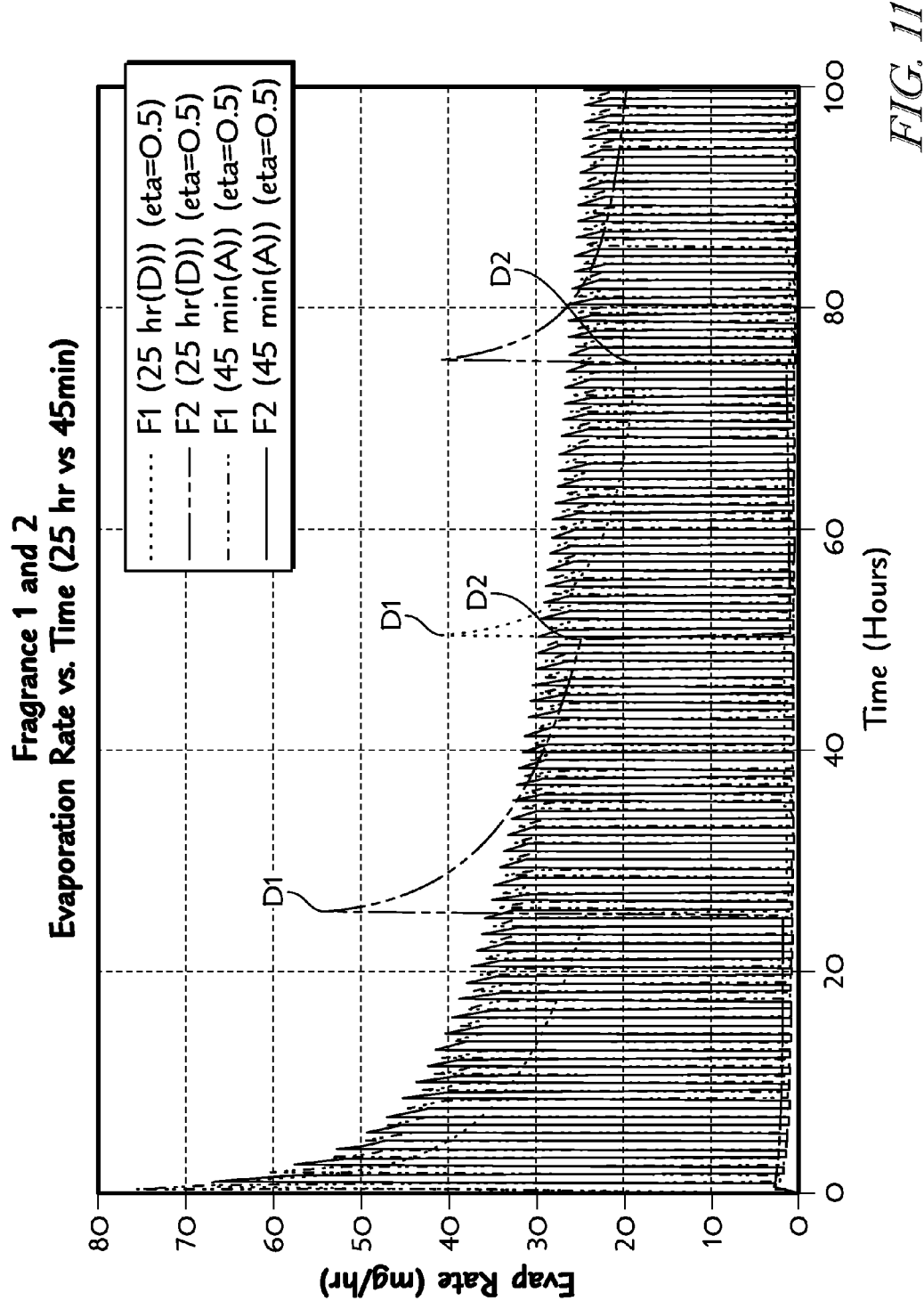
FIG. 11 is a graph similar to the graph of FIG. 10 and depicting evaporation rate versus time for the time periods of 45 minutes and 25 hours for two fragrances.

For evaporation rate versus time, the evaporation rate was calculated in milligrams per hour. The time period of (F) 1000 hours was included as a benchmark for a dispenser without alternating fragrances and which includes the steady state operation of only one of the heating blocks. FIG. 10 depicts the evaporation rate versus time for the time periods (A) through (F) for a single fragrance (with the second fragrance removed from the graph for clarity) and FIG. 11 depicts the evaporation rate versus time for the time periods (A) 45 minutes and (D) 25 hours for both fragrances.

Referring to FIG. 10, the time period (F) of 1000 hours approaches a steady state of a little less than 20 milligrams per hour around 50 hours of operation. The time period of (A) 45 minutes has peaks or primary evaporation rates A1 that follow a steady decline and valleys or secondary evaporation rates A2 that follow a similar decline. Peaks as discussed in relation to FIGS. 10 and 11 refer to an initial peak in evaporation rate of a fragrance after an associated heater has been activated. Generally, after reaching a peak evaporation rate, the evaporation rate decreases prior to deactivation of the heater. Valleys as discussed in relation to FIGS. 10 and 11 refer to the final evaporation rate prior to deactivation of the associated heater. After deactivation, the evaporation rate drops to almost zero for a period of time until the associated heater is again activated and another peak occurs. The evaporation rate never drops to zero because there is always some passive emission from the associated wick. During the testing associated with FIGS. 10 and 11, the power input to the heater was held constant during each activation period.

Referring to FIG. 10, at about 13.6 hours the peak is about 39.6 milligrams per hour and the valley is about 35.9 milligrams per hour. The peaks and valleys therefore differ by about 9.3% ((39.6 mg/hr–35.9 mg/hr)/39.6 mg/hr). Similarly, at about 40.6 hours, the peak is about 30.6 milligrams per hour and the valley is about 27.3 milligrams per hour. The difference between the peaks and valleys is therefore about 10.8%. The time period (A) therefore has a variance between peaks and valleys of about 10%.

Still referring to FIG. 10, the time period (B) 2 hours has peaks B1 and valleys B2 that have a variance of at least about 30%. For example, at about 8.0 hours, the peak is about 50.8 milligrams per hour and the valley is about 36.1 milligrams per hour (variance of about 28.9%) and the period at 40.0 hours has a peak of about 35.9 milligrams per hour and a valley of about 25.1 milligrams per hour (variance of about 30.1%). The time period (C) 10 hours has peaks C1 and valleys C2 with a variance of at least about 40%. For example, the period starting at about 20.3 hours has a peak of about 44.7 milligrams per hour and a valley of about 25.7 milligrams per hour (variance of about 42.5%) and the period starting at about 40.3 hours has a peak of about 39.2 milligrams per hour and a valley of about 22.2 milligrams per hour (variance of about 43.4%). The time period (D) 25 hours has peaks D1 and valleys D2 that have a variance of at least about 50%. For example, as seen in FIG. 11, the period beginning at about 25.0 hours has a peak of about 54.1 milligrams per hour and a valley of about 25.0 milligrams per hour (variance of about 53.8%) and the period beginning at about 50.4 hours has a peak of about 40.9 milligrams per hour and a valley of about 18.7 milligrams per hour (variance of about 54.3%).

In illustrative embodiments, the variance between peaks and valleys of fragrance emission is at least about 20%. In alternative illustrative embodiments, the variance between peaks and valleys of fragrance emission is at least about 25%. In still alternative illustrative embodiments, the variance between peaks and valleys of fragrance emission is at least about 30%, at least about 40%, or at least about 50%. It has been discovered that the greater the variance in evaporation rate, the more noticeable the different fragrance is to a user. More specifically, comparing the time period (A) 45 minutes to the time period (D) 25 hours, the small variances in the evaporation rate as seen in FIG. 11 for (A) allows a user to become accustomed to the generally static evaporation rate of a fragrance. In contrast, the dynamic evaporation rate provided by the time period (D) provides a large fluctuation in evaporation rate, despite the power input to the heater during each activation period being held constant and the air change rate in the room being held constant throughout the simulation process.

Figure 12:
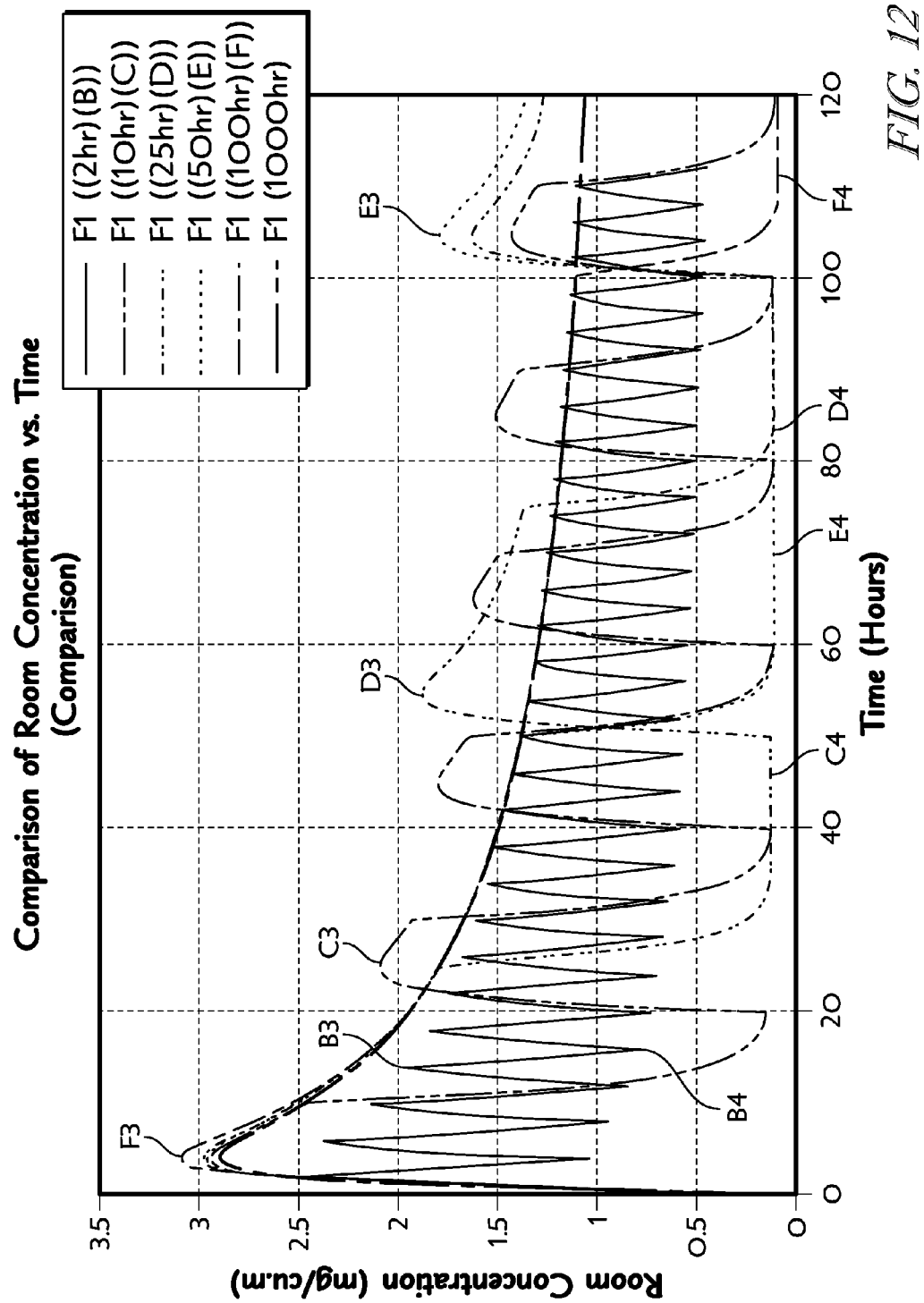
FIG. 12 is a graph depicting room concentration (in milligrams per cubic meter) versus time (in hours) for time periods of 2 hours, 10 hours, 25 hours, 50 hours, 100 hours, and 1000 hours for a single fragrance.

For room concentration versus time, the room concentration was calculated in milligrams per cubic meter ($mg/m^3$). As noted above, a standard model room volume of about 28 cubic meters ($m^3$) (10 feet by 12 feet by 8.25 feet, which is about 988 cubic feet) and a standard air change rate of 0.5 (changes per hour) were used. An ordinary differential equation integration method was used with $\beta=0.5$ (and the Crank Nicolson method, which is $2^{nd}$ order accurate). Referring to FIG. 12, room concentration versus time is shown for time periods (B) through (F) and FIG. 13 depicts room concentration versus time for time periods (A) 45 minutes and (D) 25 hours.

Referring to FIG. 12, the time period (F) is shown as a benchmark for a dispenser without alternating fragrances and which includes the steady state operation of only one of the heating blocks. In comparison to the time period (F), time periods less than 10 hours (i.e., (B) 2 hours) have room concentrations that increase after activation of a heater to a peak room concentration B3 and then decrease after deactivation to a base room concentration B4. As an example, the labeled peak room concentration B3 at 14 hours and base room concentration B4 at 16 hours are 1.95 $mg/m^3$ and 0.78 $mg/m^3$, respectively. At 14 and 16 hours, the room concentrations for the steady state curve of (F) are about 2.20 $mg/m^3$ and about 2.10 $mg/m^3$, respectively. The peak room concentrations for (B) generally follow the steady state curve for (F) and the base room concentrations follow a similar curve with the base leveling out at about 0.5 milligrams per cubic meter. In sharp contrast, time periods of about 10 hours and greater (time periods (C) through (F)) have peak room concentrations C3, D3, E3, F3 that are greater than the steady state room concentration of (F). More specifically, the room concentrations for C3, D3, E3, and F3 are about 2.08 $mg/m^3$, 1.86 $mg/m^3$, 1.78 $mg/m^3$, and 2.93 $mg/m^3$, respectively, at 25 hours, 55 hours, 104 hours, and 4.3 hours, respectively. At 25 hours, 55 hours, 104 hours, and 4.3 hours, the room concentrations for the steady state curve of (F) are about 1.78 $mg/m^3$, 1.33 $mg/m^3$, 1.10 $mg/m^3$, and 2.93 $mg/m^3$. Longer time periods correlate to greater peak room concentrations, which equate to more noticeability of the fragrances.

In illustrative embodiments, the peak room concentration is at least about 0.2 $mg/m^3$ greater than the steady state room concentration (F). In alternative illustrative embodiments, the peak room concentration is at least about 0.25 $mg/m^3$, at least about 0.3 $mg/m^3$, at least about 0.35 $mg/m^3$, or at least about 0.4 $mg/m^3$ greater than the steady state room concentration (F). As seen in FIGS. 12 and 13, the room concentration for the time period (C) 10 hours is about 0.3 $mg/m^3$ greater than the steady state room concentration, the room concentration for the time period (D) 25 hours is about 0.5 $mg/m^3$ greater than the steady state room concentration (F), and the room concentration for the time period (E) 50 hours is about 0.7 $mg/m^3$ greater than the steady state room concentration (F).

Figure 13:
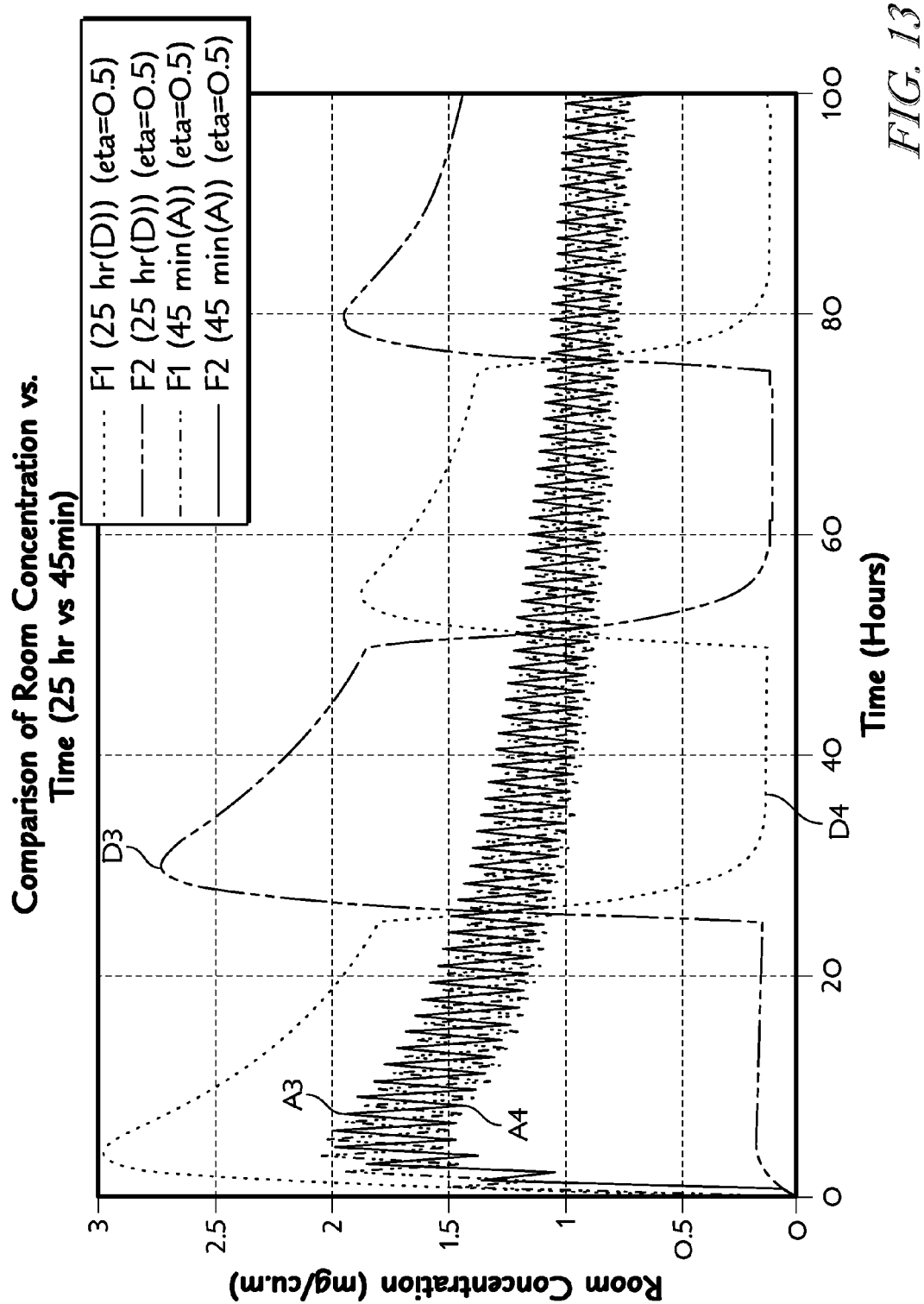
FIG. 13 is a graph similar to the graph of FIG. 12 and depicting room concentration versus time for a time period of 45 minutes and the time period of 25 hours for two fragrances.

As seen in FIGS. 12 and 13, time periods of 10 hours and greater (time periods (C) through (F)) also have base room concentrations C4, D4, E4, F4 that are much less than those for shorter time periods (for example, (A) 45 minutes and (B) 2 hours). For example, the base room concentration C4, D4, E4, F4 for the time periods (C) through (F) level off to about 0.13 $mg/m^3$, 0.12 $mg/m^3$, 0.12 $mg/m^3$, and 0.12 $mg/m^3$, respectively, before the heating block associated therewith is again activated.

In illustrative embodiments, the base room concentration is at or below about 0.45 $mg/m^3$. In alternative illustrative embodiments, the base room concentration is at or below about 0.4 $mg/m^3$, at or below about 0.35 $mg/m^3$, at or below about 0.3 $mg/m^3$, at or below about 0.25 $mg/m^3$, or at or below about 0.2 $mg/m^3$.

In illustrative embodiments, a variance between the peak room concentration and the base room concentration is at least about 1 mg/m$^3$. In other illustrative embodiments, the variance between the peak room concentration and the base room concentration is at least about 1.2 mg/m$^3$, at least about 1.4 mg/m$^3$, or at least about 1.6 mg/m$^3$.

It has been discovered that greater variances in room concentration, which equates to greater peak room concentrations and lesser base room concentrations, result in more noticeability of the fragrance by a user. More specifically, comparing the time period (A) 45 minutes to the time period (D) 25 hours, the small variances in the room concentration as seen in FIG. 13 for (A) allow a user to become accustomed to the generally static room concentration. In contrast, the dynamic room concentrations for the time period (D) provide a large fluctuation rate in the room concentration, thereby providing more noticeability to the emitted fragrance.

In illustrative embodiments, a room concentration of a first fragrance and a room concentration of a second fragrance are simultaneously at a level of 0.5 mg/m$^3$ or greater for less than or equal to about 90% of a first period of time during which the first fragrance is emitted and for less than or equal to about 90% of a second period of time during which the second fragrance is emitted. As seen in FIG. 13, for the time period (D) 25 hours, the time during which the room concentrations of both the first fragrance and the second fragrance are at least 0.5 mg/m$^3$ is less than about 3 hours (between about 25.4 and about 28.1 hours, between about 50.5 and about 53.1 hours, and between about 75.5 and about 77.4 hours). The first and second fragrances are simultaneously at a level of at least 0.5 mg/m$^3$ for less than 6% of each of the first and second time periods (1.5 hours/25 hours) or less than 12% of a cycle (which includes both the first and second time periods). In contrast, as further seen in FIG. 13, for the time period (A) 45 minutes, the time during which the room concentrations of both the first and second fragrances are simultaneously at a level of at least 0.5 mg/m$^3$ is continuous. More specifically, the room concentrations of the first and second fragrances are continuously above 0.5 mg/m$^3$, therefore the room concentrations of the first and second fragrances are simultaneously at a level of 0.5 mg/m$^3$ for 100% of each of the first and second periods and 100% of a cycle.

In alternative illustrative embodiments, a room concentration of a first fragrance and a room concentration of a second fragrance are simultaneously at a level of at least 0.5 mg/m$^3$ for less than or equal to about 90%, 80%, 70%, 60%, 50%, 40%, 30%, or 20% of the first period of time during which the first fragrance is emitted and for less than or equal to about 90%, 80%, 70%, 60%, 50%, 40%, 30%, or 20% of the second period of time during which the second fragrance is emitted. Similarly, the room concentrations of the first and second fragrances may be simultaneously at a level of at least 0.5 mg/m$^3$ for less than or equal to about 80%, 70%, 60%, 50%, 40%, 30%, or 20% of a cycle.

It has been discovered that simultaneous room concentrations of at least 0.5 mg/m$^3$ are not desirable and produce unwanted mixing of fragrance. It is therefore desirable to minimize simultaneous room concentrations of at least 0.5 mg/m$^3$. Less mixing of fragrances increases noticeability and perception of the individual fragrances. When users are constantly smelling two fragrances together, those fragrances blend together to create a single, blended fragrance that is perceived by a user. While the first and second fragrances are continuously increasing and decreasing, they are always at a room concentration that is perceptible to a user. In contrast, when employing the time period of (D) 25 hours, the room concentrations of the fragrances drop far below 0.5 mg/m$^3$ such that, if a user perceives the fragrances that are associated with a heater that is deactivated, they are barely noticeable. In this manner, a user is able to perceive and enjoy distinct fragrances, thereby increasing noticeability of distinct fragrances.

While the methods of the present disclosure have been be discussed in relation to the dispenser 130 of FIGS. 1-4, the methods of the present disclosure may be implemented within any dispenser capable of emitting two or more volatile materials. Further, while two volatile materials are disclosed herein, the apparatuses and methods disclosed herein may be employed in conjunction with any number of the same or different volatile materials.

In addition, although the specific embodiments herein refer to fragrances rather than volatile materials, it is to be understood that any type of volatile material that are susceptible to habituation and/or lose their efficacy after a period of time. Such volatile materials include, but are not limited to, odor eliminators, fragrances, insecticides, insect repellants, insect attractants, disinfectants, positive fragrancing active materials, air purifiers, aromatherapy scents, antiseptics, deodorizers, air fresheners, or the like, and combinations thereof.

Any of the embodiments described herein may be modified to include any of the structures or methodologies disclosed in connection with other embodiments.

Further, although directional terminology, such as front, back, top, bottom, upper, lower, etc. may be used throughout the present specification, it should be understood that such terms are not limiting and are only utilized herein to convey the orientation of different elements with respect to one another.

All documents cited in the Detailed Description are, in relevant part, incorporated herein by reference; the citation of any document is not to be construed as an admission that it is prior art with respect to the present disclosure.

INDUSTRIAL APPLICABILITY

The present disclosure provides methods of operating a dispenser having two or more volatile materials, wherein the methods decrease habituation, yet allow a user to sense and enjoy each of the volatile materials.

Numerous modifications to the present disclosure will be apparent to those skilled in the art in view of the foregoing description. Accordingly, this description is to be construed as illustrative only and is presented for the purpose of enabling those skilled in the art to make and use the embodiments of the disclosure and to teach the best mode of carrying out same. The exclusive rights to all modifications which come within the scope of the appended claims are reserved.

We claim:

1. A method of alternatingly emitting two or more volatile materials, the method including the steps of:
  (a) activating a first heater to emit a first volatile material;
  (b) emitting the first volatile material for a first period of time including the steps of:
    emitting the first volatile material at a first primary evaporation rate; and
    emitting the first volatile material at a first secondary evaporation rate after evaporation of the first volatile material at the first primary evaporation rate;

wherein the first secondary evaporation rate is less than the first primary evaporation rate and the power inputted to the first heater is held constant when the first heater is active;
(c) deactivating the first heater;
(d) activating a second heater to emit a second volatile material;
(e) emitting the second volatile material for a second period of time including the steps of:
emitting the second volatile material at a second primary evaporation rate; and
emitting the second volatile material at a second secondary evaporation rate after evaporation of the second volatile material at the second primary evaporation rate;
wherein the second secondary evaporation rate is less than the second primary evaporation rate and the power input to the second heater is held constant when the second heater is active;
(f) deactivating the second heater; and
repeating the steps of (a) through (f).

2. The method of claim 1, wherein the step of activating the heater occurs at the same time as or after the first heater has been deactivated.

3. The method of claim 1, wherein the step of activating the second heater occurs before the first heater has been deactivated.

4. The method of claim 1, wherein a variance between the first primary evaporation rate and the first secondary evaporation rate is at least about 20% or a variance between the second primary evaporation rate and the second secondary evaporation rate is at least about 20%.

5. The method of claim 4, wherein the variance between the first primary evaporation rate and the first secondary evaporation rate is at least about 25% or the variance between the second primary evaporation rate and the second secondary evaporation rate is at least about 25%.

6. The method of claim 1, wherein the first and second time periods are each between about 10 hours and about 50 hours.

7. The method of claim 6, wherein the first and second time periods are each between about 20 and about 40 hours.

8. A method of alternatingly emitting two or more volatile materials, the method including the steps of:
(a) activating a first heater to emit a first volatile material;
(b) emitting the first volatile material for a first time period of time including the steps of:
during a first portion of the first time period, emitting the first volatile material such that a first primary room concentration is achieved; and
during a second portion of the first time period, emitting the first volatile material such that a first secondary room concentration is achieved;
wherein the first secondary room concentration is less than the first primary room concentration and the first secondary room concentration occurs after the first primary room concentration;
(c) deactivating the first heater;
(d) activating a second heater to emit a second volatile material; and
(e) emitting the second volatile material for a second period of time including the steps of:
during a first portion of the second time period, emitting the second volatile material such that a second primary room concentration is achieved; and
during a second portion of the second time period, emitting the second volatile material such that a second secondary room concentration is achieved;
wherein the second secondary room concentration is less than the second primary room concentration and the second secondary room concentration occurs after the second primary room concentration;
(f) deactivating the second heater; and
repeating the steps of (a) through (f), wherein the room concentration of the first volatile material peaks at the first primary room concentration and trends downwardly until the first secondary room concentration at the point where the first heater is deactivated and the room concentration of the second volatile material peaks at the second primary room concentration and trends downwardly until the second secondary room concentration at the point where the second heater is deactivated.

9. The method of claim 8, wherein the step of activating the second heater occurs at the same time as or after the first heater has been deactivated.

10. The method of claim 8, wherein the step of activating the second heater occurs before the first heater has been deactivated.

11. The method of claim 8, wherein a variance between the first primary room concentration and the first secondary room concentration is at least about 1.0 mg/m$^3$ or a variance between the second primary room concentration and the second secondary room concentration is at least about 1.0 mg/m$^3$.

12. The method of claim 11, wherein a variance between the first primary room concentration and the first secondary room concentration is at least about 1.4 mg/m$^3$ or a variance between the second primary room concentration and the second secondary room concentration is at least about 1.4 mg/m$^3$.

13. The method of claim 8, wherein an overall room concentration of the first volatile material and an overall room concentration of the second volatile material are simultaneously at a level of greater than or equal to 0.5 milligrams per cubic meter for less than or equal to about 90% of the first time period and for less than or equal to about 90% of the second time period.

14. The method of claim 13, wherein the overall room concentration of the first volatile material and the overall room concentration of the second volatile material are simultaneously at a level of greater than or equal to 0.5 milligrams per cubic meter for less than or equal to about 50% of the first time period and for less than or equal to about 50% of the second time period.

15. A method of alternatingly emitting two or more volatile materials, the method including the steps of:
(a) activating a first heater to emit a first volatile material;
(b) emitting the first volatile material for a first time period;
(c) deactivating the first heater;
(d) activating a second heater to emit a second volatile material, wherein the second heater is activated prior to deactivation of the first heater, at the same time as deactivation of the first heater, or after deactivation of the first heater;
(e) emitting the second volatile material for a second time period;
(f) deactivating the second heater; and
repeating the steps of (a) through (f);
wherein, prior to repeating step (a), a room concentration of the first volatile material is reduced to a level of less than or equal to about 0.4 milligrams per cubic meter and, prior to repeating step (d), a room concentration of the second volatile material is reduced to a level of less than or equal to about 0.4 milligrams per cubic meter and wherein the first heater is supplied with a constant power input when the first heater is active and the second heater is supplied with a constant power input when the second heater is active.

16. The method of claim 15, wherein, prior to repeating step (a), the room concentration of the first volatile material is reduced to a level of less than or equal to about 0.2 milligrams per cubic meter and, prior to repeating step (d), the room concentration of the second volatile material is reduced to a level of less than or equal to about 0.2 milligrams per cubic meter.

17. The method of claim 15, wherein the room concentration of the first volatile material and the room concentration of the second volatile material are simultaneously at a level of greater than or equal to 0.5 milligrams per cubic meter for less than or equal to about 90% of the first time period and for less than or equal to about 90% of the second time period.

18. The method of claim 17, wherein the room concentration of the first volatile material and the room concentration of the second volatile material are simultaneously at a level of greater than or equal to 0.5 milligrams per cubic meter for less than or equal to about 50% of the first time period and for less than or equal to about 50% of the second time period.

* * * * *